United States Patent [19]

Martin et al.

[11] Patent Number: 5,741,961
[45] Date of Patent: Apr. 21, 1998

[54] QUARTZ RESONATOR FLUID DENSITY AND VISCOSITY MONITOR

[75] Inventors: Stephen J. Martin; James J. Wiczer; Richard W. Cernosek, all of Albuquerque; Gregory C. Frye, Cedar Crest; Charles T. Gebert, Albuquerque; Leonard Casaus, Bernalillo; Mary A. Mitchell, Tijeras, all of N. Mex.

[73] Assignee: Sandia Corporation, Albuquerque, N. Mex.

[21] Appl. No.: 108,397

[22] Filed: Aug. 18, 1993

[51] Int. Cl.⁶ .................................................. G01N 9/00
[52] U.S. Cl. ............................................................ 73/32 R
[58] Field of Search ...................... 73/290 R, 290 V, 73/32 R, 30.04; 331/116 R, 65, 158; 810/316

[56] References Cited

U.S. PATENT DOCUMENTS

| | | | |
|---|---|---|---|
| 3,829,217 | 8/1974 | Johnson et al. | 356/70 |
| 3,905,702 | 9/1975 | Johnson | 356/70 |
| 4,129,031 | 12/1978 | Tehon et al. | 73/32 A |
| 4,496,287 | 1/1985 | Nelson et al. | 417/63 |
| 4,550,591 | 11/1985 | Cox et al. | 73/28 |
| 4,565,942 | 1/1986 | Sakai et al. | 310/338 |
| 4,570,069 | 2/1986 | Gager | 250/343 |
| 4,629,334 | 12/1986 | Hockstein | 374/103 |
| 4,644,177 | 2/1987 | Barabino | 250/577 |
| 4,646,070 | 2/1987 | Yasuhara et al. | 340/603 |
| 4,649,711 | 3/1987 | Sibley et al. | 62/129 |
| 4,658,638 | 4/1987 | Plahmer | 73/7 |
| 4,677,847 | 7/1987 | Sawatari et al. | 73/64 |
| 4,706,193 | 11/1987 | Imajo et al. | 364/424 |
| 4,733,556 | 3/1988 | Meitzler et al. | 73/64 |
| 4,734,682 | 3/1988 | Bond, Jr. | 340/614 |
| 4,741,200 | 5/1988 | Hammerle | 73/54 |
| 4,764,671 | 8/1988 | Park | 250/227 |
| 4,782,332 | 11/1988 | Cipris et al. | 340/603 |
| 4,784,771 | 11/1988 | Wathen et al. | 210/636 |
| 4,792,791 | 12/1988 | Cipris et al. | 340/603 |
| 4,793,977 | 12/1988 | Morris | 422/55 |
| 4,796,204 | 1/1989 | Inoue | 364/550 |
| 4,804,935 | 2/1989 | Hori et al. | 338/25 |
| 4,839,831 | 6/1989 | Imajo et al. | 364/550 |
| 4,970,492 | 11/1990 | King | 340/450.3 |
| 5,053,745 | 10/1991 | Sasaki et al. | 340/450.3 |
| 5,076,094 | 12/1991 | Frye et al. | 73/19.03 |
| 5,089,780 | 2/1992 | Megerle | 324/448 |
| 5,201,215 | 4/1993 | Grandstaff et al. | 73/54.41 |
| 5,416,448 | 5/1995 | Wessendorf | 331/116 R |

FOREIGN PATENT DOCUMENTS 442 314  1/1991  European Pat. Off. .

OTHER PUBLICATIONS

Martin, S. J. et al. 1993 IEEE International Frequency Control Symposium, "Measuring Liquid Properties with Smooth–and Textured–Surface Resonators" (Jun. 2–4 1993), pp. 603–608.

Stephen J. Martin, et al., "Characterization of a Quartz Crystall Microbalance with Simultaneous Mass and Liquid Loading," *Analytical Chemistry*, Vol. 63, No. 20, pp. 2272–2281 (1991).

*Primary Examiner*—Hezron E. Williams
*Assistant Examiner*—Christine K. Oda

[57] ABSTRACT

A pair of thickness-shear mode resonators, one smooth and one with a textured surface, allows fluid density and viscosity to be independently resolved. A textured surface, either randomly rough or regularly patterned, leads to trapping of liquid at the device surface. The synchronous motion of this trapped liquid with the oscillating device surface allows the device to weigh the liquid; this leads to an additional response that depends on liquid density. This additional response enables a pair of devices, one smooth and one textured, to independently resolve liquid density and viscosity; the difference in responses determines the density while the smooth device determines the density-viscosity product, and thus, the pair determines both density and viscosity.

48 Claims, 13 Drawing Sheets

5,741,961

QUARTZ RESONATOR FLUID DENSITY AND VISCOSITY MONITOR

GOVERNMENT RIGHTS

The U.S. Government has a paid-up license to this invention and the right in limited circumstances to require the patent owner to license others on reasonable terms.

BACKGROUND OF THE INVENTION

1. Field of the Invention (Technical Field)

The invention relates to sensors and more particularly to sensors capable of making real-time in situ measurements of liquid density and viscosity. These properties are important parameters in many lubricants, working fluids, chemical processes, batteries and the like.

2. Background Art

Presently, liquid densities can be measured most conveniently using liquid densitometers. These use liquid quantities on the order of 1 ml, providing a measurement accuracy on the order of 0.01%. These devices typically cannot be used for in situ measurements of density since the device cannot be easily operated in a closed container or environment.

A number of devices exist for measurement of liquid viscosities. Falling-ball viscometers provide a measurement accuracy of about 2%, but require a large sample volume (10 ml) and are not suitable for in situ measurements. Miniature devices using electromagnetically driven plungers are available for in situ measurements of viscosity. Capillary tube viscometers can provide real-time measurements, but require a side stream tube in the process and are not suitable for in situ monitoring.

The present invention has the advantage that it simultaneously provides independent measurements of both liquid density and viscosity. In addition, the invention requires extremely small sample volumes—on the order of 0.01 ml or less. The sensor is a solid-state apparatus, having no macroscopic moving parts, and can be easily inserted into a closed chamber to provide in situ measurements.

The ability to simultaneously monitor both liquid density and viscosity is important in several applications. Density and viscosity often relate the condition or quality of a liquid that is subjected to a high stress environment, such as high temperatures, constant pressure or shear stress and harsh chemical interactions. One application of this invention is as an oil condition monitor. The density and viscosity of working fluids, such as engine oil, are good indicators of their functionality under certain operating conditions. A change in fluid density indicates the presence of contaminants while a change in viscosity indicates oil thickening, viscosity breakdown, or oil dilution. Viscosity changes in the lubricating oil of an internal combustion engine are measured in situ and in real-time. This negates the need to estimate the oil replacement interval solely on engine operating hours or number of vehicles miles traveled. The degradation of engine oil is dependent on several factors other than number of vehicle miles such as revolutions per minute (RPM), engine load, temperature and average distance per trip.

Presently, vehicle oil condition is determined by drawing samples from the engine crankcase and using laboratory analytical techniques to determine its condition, as indicated in "Testing Used Engine Oils", *Chevron Research Bulletin* (1983). These tests include assessment of oxidation stability, water and fuel dilution, metal particulate levels, viscosity, total acid number, and pentane insolubles. These tests are time-consuming and expensive and do not provide real-time indication of in-situ oil condition.

U.S. Pat. No. 4,742,476 to Schwartz et al., U.S. Pat. No. 4,847,768 to Schwartz, et al. and S. E. Schwartz and D. J. Smolenski, "Development of an Automatic Engine Oil-Change Indicator System," SAE Paper 870403 (1987), disclose a technique for estimating when the useful lifetime of oil is reached. This technique is based on an algorithm that estimates oil deterioration by taking into account the number of engine revolutions and the oil operating temperature. This algorithm has been tested against the analytical laboratory technique and has proven useful in estimating oil life. However, since this technique does not actually monitor oil condition during vehicle operation, it is only an estimate of the oil condition. It cannot account for irregular or non-normal conditions, such as occur when coolant, dust, water, or fuel contaminate the oil or when oil leaks or is consumed at an unusual rate. These conditions may occur due to engine malfunction or operation under extreme conditions. In addition, the algorithm does not take into account the starting condition of the oil or the type of oil, which may vary considerably. Finally, implementation of the algorithm requires a calculating means such as an on-board computer.

U.S. Pat. No. 4,565,942 to Sakai et al., discloses the use of acoustic wave techniques for monitoring liquid levels but does not teach interrogation for properties of the liquid.

U.S. Pat. Nos. 4,796,204 to Inoue, 4,733,556 to Meitzler et al., and 4,496,287 to Nelson et al., disclose methods to determine the viscosity of engine oil. Inoue teaches the monitoring of oil temperature, engine speed and engine load, entering the data into an algorithm which infers viscosity changes. Meitzler et al., discloses the use of a device and method of computing the viscosity of aging oil by measuring the dielectric constant of oil with a capacitance/oscillator circuit and comparing the data with new oil. Nelson, et al., discloses a sensor for measuring the opposition of the fluid to its own physical displacement by mechanical displacement of a spring-mass system, which is related to certain properties such as viscosity. None of these references teach the use of ultrasonic sensors for measuring the viscosity and density of a liquid.

Several patents relate methods for determining the quality or aging of engine oil or like liquids. These patents include U.S. Pat. No. 3,829,217 to Johnson, et al., U.S. Pat. No. 3,905,702 to Johnson, U.S. Pat. No. 4,570,069 to Gager, and U.S. Pat. No. 4,649,711 to Sibley, et al., which describe measurements of optical transmission (both visible and infrared); U.S. Pat. No. 4,644,177 to Barabino and U.S. Pat. No. 4,764,671 to Park describe the use of optical refractive index; U.S. Pat. No. 4,646,070 to Yasuhara, et al., and U.S. Patent No. 4,733,556 to Meitzler, et al., disclose the use of a dielectric constant; U.S. Pat. No. 4,629,334 to Hochstein, U.S. Pat. No. 4,635,473 to Hochstein, U.S. Pat. No. 4,782,332 to Cipris, et al., and U.S. Pat. No. 5,089,780 to Megerle disclose methods to utilize electrical resistance or conductivity; and U.S. Pat. No. 4,550,591 to Cox, et al., describes monitoring filtered particulates.

U.S. Pat. No. 4,471,200 to Hammerle uses a quartz crystal to sense properties of a contacting fluid. Although the title of the patent claims to measure viscosity of the contacting liquid, the device actually measures the density-viscosity product, as explained in the text. It does not disclose the concurrent measurement and inclusion of the liquid temperature which is a prime determinative factor in sensing the condition of fluids such as engine oil. This device fails to provide correct indication of viscosity changes when density changes are also occurring, e.g., when engine oil is contaminated with soot, metal particles and other fluids.

U.S. Pat. No. 4,129,031 to Tehon et al., discloses a device that uses vibrating cups for measuring liquid density. The device does not use monolithic piezoelectric crystal technology and is thus not suitable for integration with the piezoelectric resonator to form a device capable of extracting density and viscosity. Furthermore, the large size of this device makes it unsuitable for use as an in-situ sensor of liquid density.

SUMMARY OF THE INVENTION
(DISCLOSURE OF THE INVENTION)

In accordance with the present invention, there is provided a method and apparatus for monitoring the condition of fluids, more particularly the independent measurement of density and viscosity of fluids. The preferred apparatus of the invention comprises a first resonator comprising a smooth surface; a second resonator comprising a textured surface; a first measuring apparatus for measuring density of a fluid disposed on said resonators; and a second measuring apparatus for measuring viscosity of the fluid disposed on said resonators.

The preferred first resonator comprises structure for providing a product of density and viscosity of the fluid. The preferred second resonator comprises structure for providing a sum of a product of density and viscosity of the fluid plus a quantity which is proportional to density and effective thickness of the trapped fluid. The preferred first measuring apparatus comprises structure for comparing outputs of the resonators. The preferred structure for comparing outputs of the resonators comprises structure for eliminating viscosity dependence.

The preferred second measuring apparatus comprises the first measuring apparatus and an output of the first resonator. An alternative second measuring apparatus comprises the first measuring apparatus and an output of the second resonator.

The preferred measuring apparatuses comprise structure for measuring electrical responses of the resonators. An alternative structure for measuring electrical responses comprises an apparatus for measuring resonant frequencies (f). The preferred structure for measuring electrical responses comprises an apparatus for measuring crystal damping ($\Delta R_m$). Other apparatuses that can be used for measuring electrical responses comprises measuring electrical responses selected from the group consisting of admittance, impedance, reflection, and combinations thereof.

The preferred measuring apparatus for electrical responses further comprises an oscillator. An alternative apparatus for measuring electrical responses comprises structure for measuring changes in the electrical responses in a calibrating medium and upon disposition of the fluid.

The preferred first resonator also comprises a surface to minimize fluid trapping. The preferred first resonator further comprises a surface whereby an effective thickness of the trapped fluid is less than a liquid decay length (h<$\delta$) of the fluid.

The preferred second resonator also comprises a surface that traps a fixed quantity of the fluid. The preferred second resonator further comprises a textured surface to optimize an output of said second resonator. The preferred second resonator further comprises orienting ridges perpendicular to a direction of surface shear displacement. The preferred second resonator further comprises a uniformly textured surface. The preferred uniformly textured surface comprises photolithographic structure.

An alternative apparatus comprises measuring a temperature of the fluid.

The preferred apparatus comprises structure for preventing contamination buildup on the resonator surfaces. The preferred resonators further comprise piezoelectric substrates operating in a thickness shear mode. The preferred apparatus also comprises a monolithic apparatus.

The preferred apparatus for determining a condition of a fluid comprises a resonator; a fluid temperature measuring apparatus; and an output structure for providing a product of density and viscosity of fluid disposed on the resonator. The preferred output structure comprises an apparatus for measuring electrical responses of the resonator.

An alternative apparatus for measuring electrical responses comprises an apparatus for measuring resonant frequencies (f). The preferred apparatus for measuring electrical responses comprises an apparatus for measuring crystal damping ($\Delta R_m$). Other alternative apparatuses for measuring electrical responses comprise measuring an electrical response selected from the group consisting of admittance, impedance, reflection, and combinations thereof.

The preferred apparatus for measuring electrical responses also comprises an oscillator. An alternative apparatus for measuring electrical responses comprises an apparatus for measuring changes in said electrical responses measured in a calibrating medium and upon disposition of the fluid.

The preferred resonator comprises a smooth surface. The preferred smooth surface comprises a surface to minimize fluid trapping. The preferred smooth surface also comprises a surface whereby an effective thickness of the trapped fluid is less than a liquid decay length (h<$\delta$) of the fluid.

The preferred fluid temperature measuring apparatus comprises a monolithic meander-line resistor.

The preferred resonator further comprises a piezoelectric substrate operating in a thickness shear mode. The preferred apparatus further comprises a monolithic apparatus.

The preferred apparatus for measurement of fluid density and viscosity comprises a resonator comprising a textured surface; and a measuring apparatus for measuring viscosity and density of a fluid disposed on the resonator.

The preferred measuring apparatus comprises an apparatus for measuring at least two electrical responses of the resonator. The preferred apparatus for measuring at least two electrical responses comprises measuring electrical responses selected from the group consisting of resonant frequencies (f), crystal damping ($\Delta R_m$), admittance, impedance, and reflection.

The preferred apparatus for measuring at least two electrical responses also comprises an oscillator. An alternative apparatus for measuring at least two electrical responses comprises measuring changes in said electrical responses measured in a calibrating medium and upon disposition of the fluid.

The preferred resonator comprises a surface that traps a fixed quantity of the fluid. The preferred resonator also comprises a textured surface to optimize an output of the resonator.

The preferred textured surface comprises orienting ridges perpendicular to a direction of surface shear displacement. The preferred textured surface comprises a uniformly textured surface. The preferred uniformly textured surface comprises a photolithographic textured surface.

An alternative apparatus further comprises an apparatus for measuring a temperature of the fluid. The preferred apparatus further comprises structure for preventing contamination buildup on the resonator surface.

The preferred resonator further comprises a piezoelectric substrate operating in a thickness shear mode. The preferred apparatus further comprises a monolithic apparatus.

The preferred method for real-time in situ measurement of fluid density and viscosity comprising the steps of providing a first resonator comprising a smooth surface; providing a second resonator comprising a textured surface; measuring density of a fluid disposed on the resonators; and measuring viscosity of the fluid disposed on the resonators.

The preferred step of providing a first resonator comprises the resonator providing a product of density and viscosity of the fluid.

The preferred step of providing a second resonator comprises the resonator providing a sum of a product of density and viscosity of the fluid plus a quantity which is proportional to density and effective thickness of trapped fluid.

The preferred step of measuring density comprises comparing the outputs of the resonators. The preferred step of comparing outputs of the resonators comprises eliminating viscosity dependence.

The preferred step of measuring viscosity comprises measuring density and an output of the first resonator. An alternative step of measuring viscosity comprises measuring density and an output of the second resonator.

The preferred step of measuring density and viscosity also comprises measuring electrical responses of the resonators. An alternative step of measuring electrical responses comprises measuring resonant frequencies (f). The preferred step of measuring electrical responses comprises measuring crystal damping ($\Delta R_m$). Other alternatives for the step of measuring electrical responses comprise measuring electrical responses selected from the group consisting of admittance, impedance, reflection, and combinations thereof.

The preferred step of measuring electrical responses further comprises providing oscillators. An alternative step of measuring electrical responses comprises measuring changes in the electrical responses in a calibrating medium and upon disposition of the fluid.

The preferred step of providing a first resonator comprises providing a surface to minimize fluid trapping. The preferred step of providing a first resonator further comprises providing a surface whereby an effective thickness of the trapped fluid is less than a liquid decay length ($h<\delta$) of the fluid.

The preferred step of providing a second resonator comprises providing a surface that traps a fixed quantity of the fluid. The preferred step of providing a second resonator further comprises texturing the textured surface to optimize an output of the second resonator. The preferred step of providing a second resonator further comprises orienting ridges perpendicular to the direction of surface shear displacement. The preferred step of providing a resonator further comprises providing a uniformly textured surface. The preferred step of providing a uniformly textured surface comprises utilizing a photolithographic process.

An alternative method further comprises the step of measuring a temperature of the fluid.

The preferred method further comprises the step of preventing contamination buildup on the resonator surfaces.

The preferred steps of providing resonators comprise providing a piezoelectric substrate operating in a thickness shear mode.

The preferred method further comprises the step of providing a monolithic apparatus.

The preferred method for determining the condition of a fluid comprises the steps of providing a resonator; measuring a temperature of the fluid; and measuring an output that provides a product of density and viscosity of the fluid disposed on the resonator.

The preferred step of measuring an output comprises measuring electrical responses of the resonator. An alternative step of measuring electrical responses comprises measuring resonant frequencies (f). The preferred step of measuring electrical responses comprises measuring crystal damping ($\Delta R_m$). Other alternative steps of measuring electrical responses comprise measuring an electrical response selected from the group consisting of admittance, impedance, reflection, and combinations thereof.

The preferred step of measuring electrical responses further comprises utilizing an oscillator. An alternative step of measuring electrical responses comprises measuring changes in the electrical responses measured in a calibrating medium and upon disposition of the fluid.

The preferred step of providing a resonator comprises providing a smooth surface. The preferred step of providing a smooth surface comprises providing a surface to minimize fluid trapping. The preferred step of providing a smooth surface further comprises providing a surface whereby an effective thickness of the trapped fluid is less than a liquid decay length ($h<\delta$) of the fluid.

The preferred step of measuring a temperature comprises utilizing a monolithic meander-line resistor.

The preferred step of providing a resonator comprises utilizing a piezoelectric substrate operating in a thickness shear mode.

The preferred method further comprises the step of providing a monolithic apparatus.

The preferred method for measuring fluid density and viscosity comprises the steps of providing a resonator with a textured surface; and measuring viscosity and density of a fluid disposed on the resonator.

The preferred step of measuring viscosity and density comprises measuring at least two electrical responses of the resonator. The preferred step of measuring at least two electrical responses comprises measuring electrical responses from the group consisting of resonant frequencies (f), crystal damping ($\Delta R_m$), admittance, impedance, and reflection.

The preferred step of measuring at least two electrical responses further comprises utilizing an oscillator.

An alternative step of measuring at least two electrical responses comprises measuring changes in the electrical responses measured in a calibrating medium and upon disposition of the fluid.

The preferred step of providing a resonator comprises providing a textured surface that traps a fixed quantity of the fluid. The preferred step of providing a resonator further comprises texturing the textured surface to optimize an output of the resonator. The preferred step of providing a resonator further comprises orienting ridges perpendicular to a direction of surface shear displacement. The preferred step of providing a resonator further comprises providing a uniformly textured surface. The preferred step of providing a uniformly textured surface comprises utilizing a photolithographic process.

An alternative method comprises the step of measuring a temperature of the fluid. The preferred method further comprises preventing contamination buildup on the resonator surface. The preferred step of providing a resonator comprise operating a piezoelectric substrate in a thickness shear mode. The preferred method further comprises utilizing a monolithic apparatus.

The preferred apparatus for determining the condition of a fluid comprises a resonator; and a crystal damping measuring apparatus for measuring a product of density and viscosity of fluid disposed on the resonator.

The preferred measuring apparatus comprises an oscillator. The preferred crystal damping measuring apparatus comprises an apparatus for measuring changes in crystal damping ($\Delta R_m$).

An alternative apparatus for measuring changes in crystal damping ($\Delta R_m$) comprises an apparatus that measures changes in a calibrating medium and upon disposition of the fluid.

The preferred resonator comprises a smooth surface. The preferred smooth surface comprises a surface to minimize fluid trapping. The preferred smooth surface further comprises a surface whereby an effective thickness of the trapped fluid is less than a liquid decay length (h<$\delta$) of the fluid.

The preferred resonator comprises a piezoelectric substrate that operates in a thickness shear mode. The preferred apparatus further comprises a monolithic apparatus.

The preferred method of determining the condition of a fluid comprises the steps of providing a resonator; and measuring a product of density and viscosity of fluid disposed on the resonator comprising measuring crystal damping.

The preferred step of measuring a product of density and viscosity comprises an oscillator. The preferred step of measuring crystal damping comprises measuring changes in crystal damping ($\Delta R_m$). An alternative step of measuring changes in crystal damping ($\Delta R_m$) comprises measuring changes in a calibrating medium and upon disposition of the fluid.

The preferred step of providing a resonator comprises providing a smooth surface. The preferred step of providing a smooth surface comprises providing a surface to minimize fluid trapping. The preferred step of providing a smooth surface further comprises providing a surface whereby an effective thickness of the trapped fluid is less than a liquid decay length (h<$\delta$) of the fluid.

The preferred step of providing a resonator comprises providing a piezoelectric substrate operating in a thickness shear mode.

The preferred method further comprises providing a monolithic apparatus.

A primary object of the present invention is to measure the condition of fluids.

Another object of the invention is to simultaneously measure density and viscosity of a fluid.

Yet another object of the present invention is for in situ measurement of the condition of fluids.

Another object of the present invention is to measure both the density and viscosity of a fluid contacting the apparatus on either one side or both sides.

A primary advantage of the present invention is that actual measurements of density and viscosity of the fluid are made and not estimated.

Another advantage of the present invention is that it provides a simultaneous measurement fluid density and viscosity (and temperature, if a resistance temperature sensor (RTS) is included) using a small solid-state apparatus that has no macroscopic moving parts.

Another advantage of the invention is the rapid measurement of extremely small sample volumes and its suitability for inclusion in a pipe or machine for in situ monitoring of fluid properties.

Yet another advantage of the present invention is the ability to determine the condition of fluids with an inexpensive apparatus.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The apparatus and method of the present invention comprise hardware components and a process that provides an output for determination of certain conditions of fluids. The preferred embodiment of the present invention uses a pair of piezoelectric (quartz) resonators—one having smooth faces and one intentionally textured or roughened—to measure the density and viscosity of a contacting liquid. The term "textured" used throughout this disclosure refers to a textured or coarse surface that includes both random roughness (as obtained, for example, from a polishing process using abrasive particles or deposition (e.g. electrodeposition)) and regularly patterned surfaces (as obtained, for example, from photolithographic micromachining and etching techniques) that might include corrugations, regularly spaced holes, regular lattice, and other surface treatment techniques. Resonators can be constructed from a number of different piezoelectric substrate materials. Quartz was chosen in the preferred embodiment because of its widespread use, high temperature stability, well established technology base, and relatively low cost.

Figure 1:
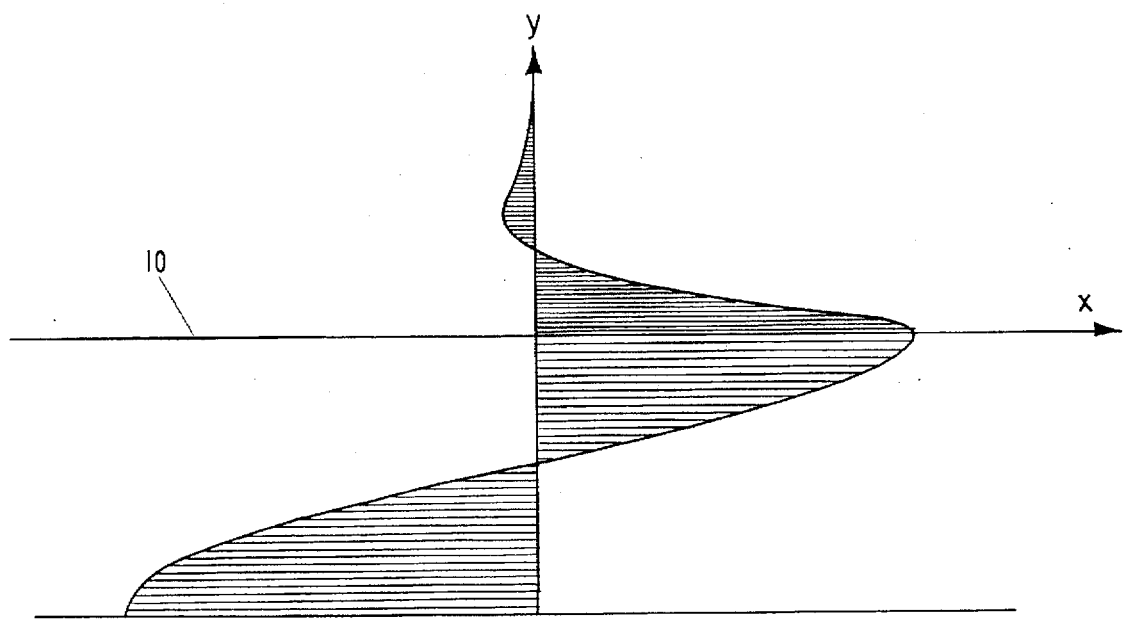
FIG. 1 is a cross-sectional displacement profile of a thickness shear mode (TSM) in an AT-cut resonator and the motion in a contacting fluid.

It is well known that thinned piezoelectric crystals can be electrically excited into mechanical resonance by applying an alternating voltage at the proper frequency to electrodes on the opposing crystal faces. There are two predominant types of modes that can be excited: compressional modes, in which the crystal is changing thickness, and thickness-shear modes (TSMs), in which the planes parallel to the crystal faces are undergoing in-plane displacement as shown in FIG. 1. The modes that are excited and the frequencies at which they are excited are determined by the crystalline material, thickness, and orientation with respect to the polished crystal faces.

For sensing liquid properties, thickness-shear modes are preferable: compressional modes couple too strongly to the contacting liquid, generating sound waves that "leak away" acoustic energy and suppress resonance; thickness-shear modes couple less strongly to the liquid and resonant characteristics are preserved. A TSM resonance can be electrically excited in certain crystallographic orientations of a piezoelectric crystal such as the AT-cut of quartz.

When a smooth shear mode resonator is operated in contact with a liquid, the oscillating surface generates plane-parallel laminar flow in the adjacent liquid, as shown in FIG. 1. The velocity field ($v_x(y)$) generated by the oscillating surface in the semi-infinite (Newtonian) liquid is described by $$v_x(y) = v_{xo} e^{-\frac{1+j}{\delta} y} \quad (1)$$

where y is the distance from the surface, $v_{xo}$ is the surface particle velocity, $j=(-1)^{1/2}$ and $\delta=(2\eta/\omega\rho)^{1/2}$ where $\rho$ and $\eta$ are the liquid density and viscosity and e is angular frequency ($\omega=2\pi f$ where f is frequency). Eq. (1) describes the behavior of liquid that is "viscously coupled" by the smooth surface. This liquid undergoes a phase lag that increases with distance from the surface, representing a critically damped shear wave that is radiated into the contacting liquid by the oscillating resonator surface; $\delta$ is the decay length of this shear wave, having, for example, a value of approximately 250 nm in water at 20° C. when the frequency is 5 MHz.

The liquid layer entrained (viscously coupled) by the oscillating smooth resonator surface leads to a decrease in the resonant frequency $\Delta f$ given as:

$$\Delta f \cong -\frac{n f_s^{3/2}}{N} \left( \frac{\rho\eta}{\pi\mu_q\rho_q} \right)^{\frac{1}{2}} \quad (2)$$

where n is the number of immersed resonator faces, $\rho_q$ and $\eta_q$ are the piezoelectric crystal's density and shear stiffness, $f_s$ is the series resonant frequency, and N is the harmonic number for the TSM resonance.

Viscous coupling to liquid also causes an increase in the motional electric resistance $\Delta R_m$ as:

$$\Delta R_m = \frac{nN\pi}{4K^2 C_o} \left( \frac{\rho\eta}{2\omega_s\mu_q\rho_q} \right)^{\frac{1}{2}} \quad (3)$$

where $\omega_s$ is the angular series resonant frequency ($\omega_s=2\pi f_s$) and $K^2$ is the electromechanical coupling coefficient for the piezoelectric crystal. The resistance $\Delta R_m$, representing power dissipated in the liquid by the oscillating surface, leads to damping of the resonance and a diminished resonant electrical admittance. The resonant admittance of the liquid-contacted apparatus is $Y(f_s) \equiv 1/\Delta R_m$; thus $\Delta R_m$ is a measure of the crystal damping caused by the liquid.

With regard to discriminating liquid properties, it is noted that these enter into both the frequency shift and motional resistance only as a product of liquid density and viscosity ($\rho\eta$). This indicates that a smooth-surfaced TSM resonator is incapable of resolving liquid density and viscosity, a critical shortcoming of all prior art. This shortcoming is remedied by including an apparatus with textured surface as explained below.

Devices with surface texture, either randomly rough or regularly patterned, trap a quantity of liquid in excess of that entrained by a smooth surface. Vertical features constrain this trapped liquid to move synchronously with the oscillating crystal surface, rather than undergoing a progressive phase lag as occurs with viscously coupled liquid (FIG. 1). This trapped liquid thus behaves as an ideal mass layer contributing an areal mass density $\rho_s=\rho h$, where $\rho$ is the density and h is the effective thickness of the trapped liquid layer-dependent upon the vertical relief of the surface texture. If this trapped liquid thickness is small compared to the liquid decay length $\delta=(2\eta/\omega\rho)^{1/2}$, then the surface is considered hydrodynamically smooth and the relative response due to liquid trapping is negligible. If h is comparable or larger than $\delta$, however, then a significant additional frequency shift arises from trapping in the textured surface that is dependent only on density and not on viscosity. Thus, a pair of resonators, one smooth and one with a textured surface, allow liquid density and viscosity to be resolved.

The resonant frequency shifts that occur upon immersion of a smooth ($\Delta f_1$) and a textured-surface ($\Delta f_2$) apparatus can be written as:

$$\Delta f_1 = -c_1 \sqrt{\rho\eta} \quad (4)$$

$$\Delta f_2 = -c_1' \sqrt{\rho\eta} - c_2 h\rho \quad (5)$$

where $c_1$, $c_1'$, and $c_2$ are constants. Viscous coupling by the smooth and textured-surface resonators gives rise to the $(\rho\eta)^{1/2}$ term. Liquid trapping in the textured surface gives rise to the second term in Eq. (5) proportional to liquid density. If the surface texture is not too large, the contribution to viscous entrainment of liquid is nearly unchanged from the smooth-surface case, i.e., $c_1' \cong c_1$.

From Eqs. (4) and (5), the liquid density can be obtained from the difference in responses measured between the smooth and textured resonators upon immersion:

$$p = \frac{c_1'\Delta f_1 - c_1 \Delta f_2}{c_1 c_2 h} \quad (6)$$

Having determined liquid density, the response of the smooth apparatus can then be used in Eq. (4) to determine liquid viscosity:

$$\eta = \frac{(\Delta f_1)^2}{c_1^2 \rho} = \frac{c_2 h (\Delta f_1)^2}{c_1(c_1'\Delta f_1 - c_1\Delta f_2)} \quad (7)$$

Alternatively, if the motional electrical resistance $R_m$ is measured, the change in motional resistance due to liquid loading can be given as $\Delta R_m = c_3(\eta\rho)^{1/2}$. Liquid viscosity can then be determined from this parameter:

$$\eta = \frac{1}{\rho}\left(\frac{\Delta R_m}{c_3}\right)^2. \quad (8)$$

Figures 2A, 2B:
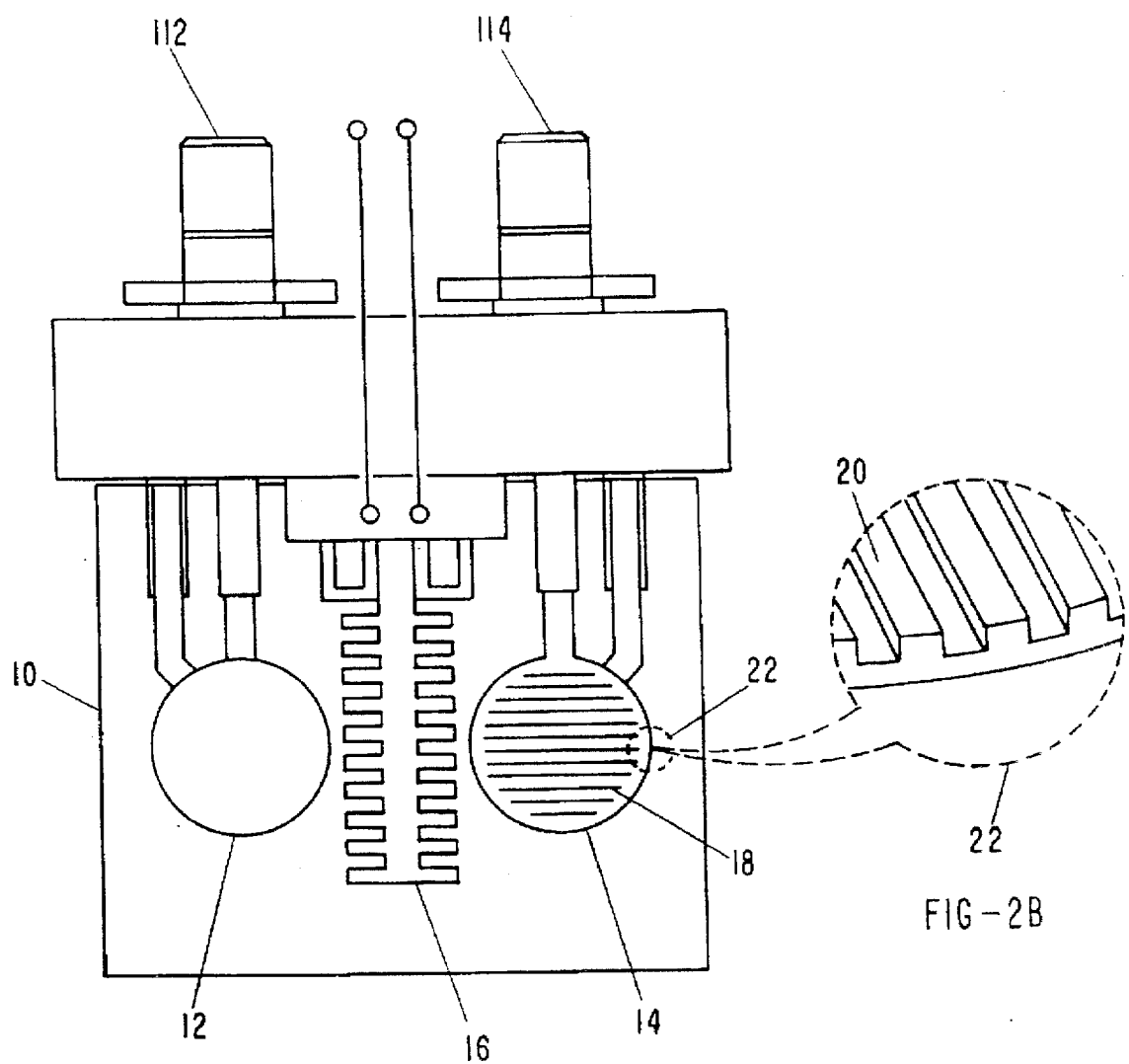
FIG. 2a depicts the preferred monolithic sensor.
FIG. 2b is an enlarged view of the corrugation pattern of the textured resonator.

FIG. 2a shows the preferred monolithic quartz sensor 10 that includes smooth 12 and textured 14 thickness shear mode (TSM) resonators to measure fluid density and viscosity. Since liquid properties (especially viscosity) are temperature dependent, a meander-line resistance temperature sensor (RTS) 16 is included for measuring liquid temperature. Other temperature sensing methods that are well known can be employed. Texture 18 in the form of a surface corrugation is formed on one resonator 14. This can be done by electrodepositing periodic gold ridges on top of the gold electrodes or the like. In order to trap liquid and insure that it moves synchronously with textured surface 18, ridges 20 as shown in FIG. 2b are preferably oriented perpendicular to the direction of surface shear displacement the +X crystalline direction.

Figure 3:
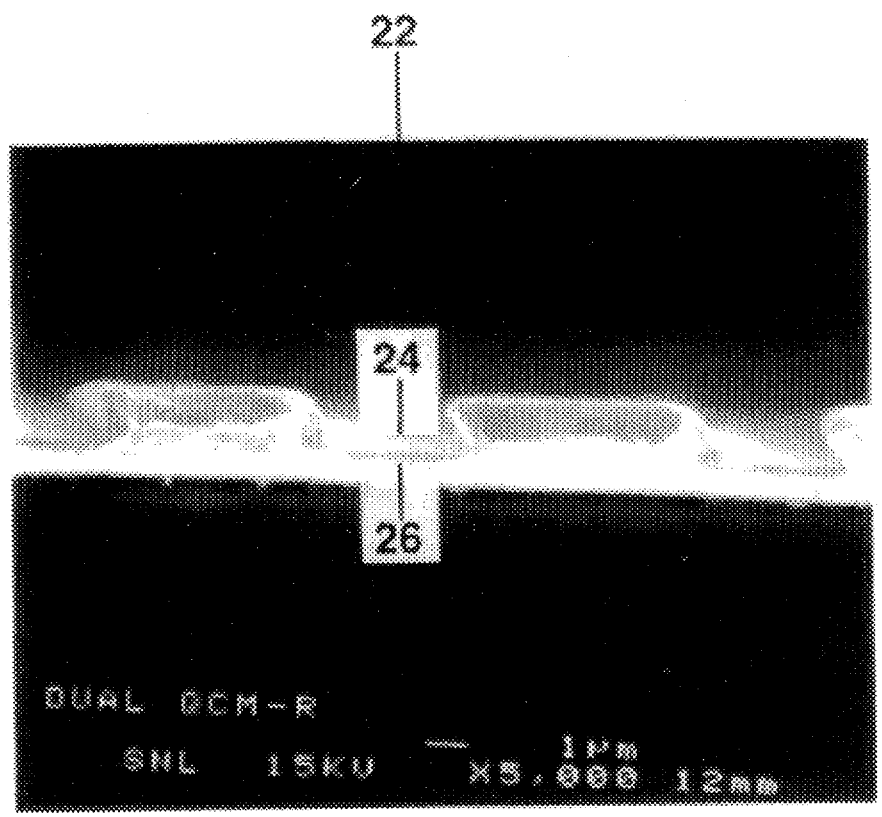
FIG. 3 is a scanning electron microscope (SEM) micrograph of the preferred surface corrugation.

In fabricating dual-resonator 10, a Cr/Au (30 nm/200 nm) metallization layer, or the like, is first deposited on both sides of an optically polished AT-cut quartz wafer (other materials and crystal cuts can also be used). This metallization layer can be patterned (e.g. photolithographically) to form the resonator electrodes (both sides) and meander-line RTS 16 (one side). A periodic resist pattern is formed on both electrodes of textured resonator 14. Gold, or a similar material is electrodeposited in the exposed electrode regions to a thickness of approximately 1.5 µm. When the photoresist is removed, corrugation pattern 22 remains as shown in FIG. 3, with trapezoidal cavities 24 approximately 4.6 µm wide at base 26 that are well suited for trapping liquid. Although this embodiment specifically describes this particular type of texture, other textures can be utilized.

Figure 4:
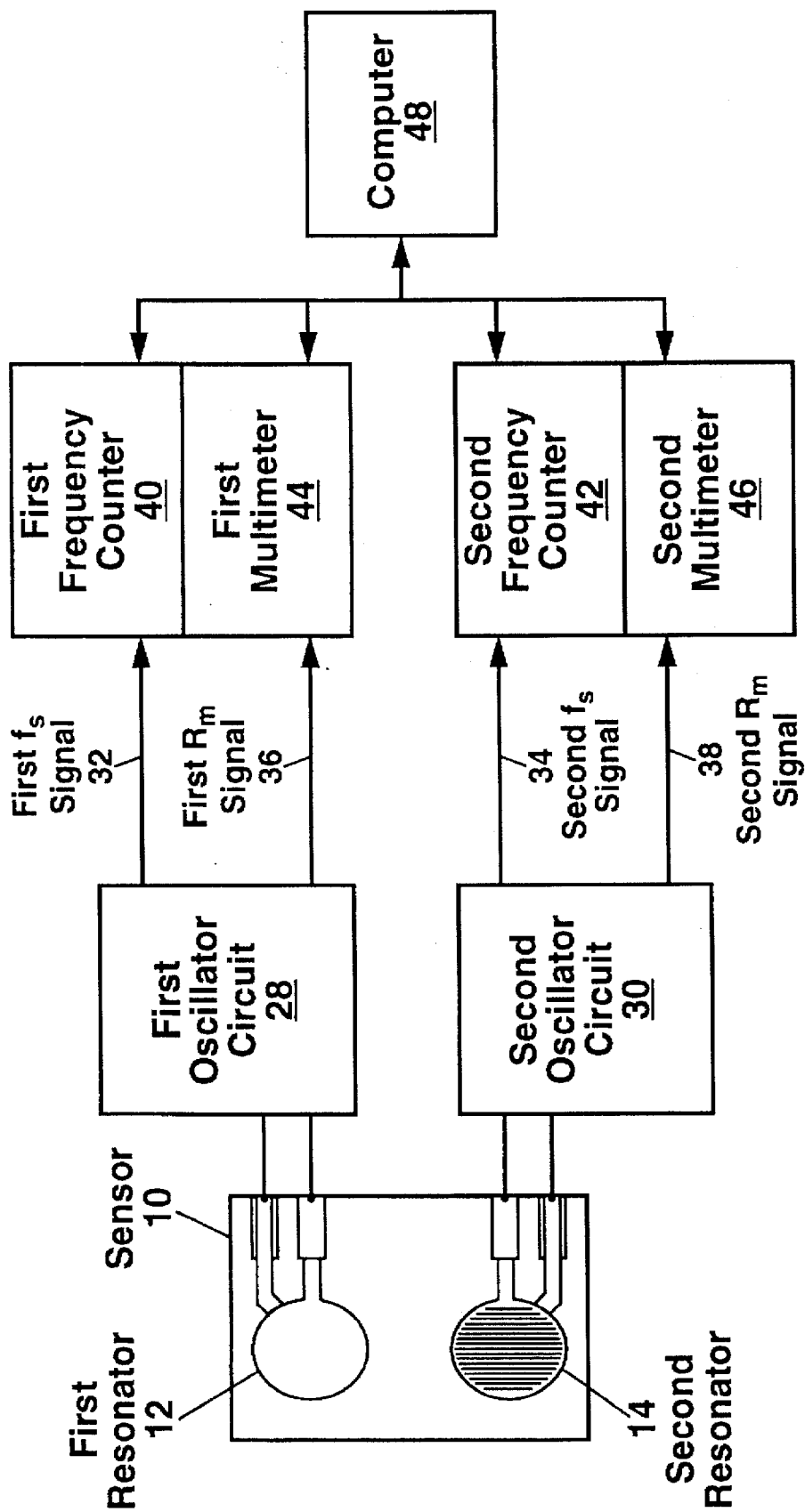
FIG. 4 schematically illustrates the operation of the preferred liquid density and viscosity sensor.

Dual-resonator 10 is instrumented for liquid density and viscosity determination as shown in FIG. 4. Resonators 12 and 14 are driven by independent oscillator circuits 28 and 30 that provide two outputs each; and RF signals that tracks $f_s$ 32 and 34 and DC voltages proportional to $R_m$ 36 and 38. The RF outputs from the oscillators are read by frequency counter 40 and 42 while DC voltages and resistance are read by multimeters 44 and 46. These signals are input to computer 48 or similar computing apparatus. The baseline responses are determined by measuring $f_s$ 32 and 34 and $R_m$ 36 and 38 for each apparatus 12 and 14 before immersion. Baseline responses can also be measured in fluid media with known densities and viscosities. Changes in responses are then measured for the smooth ($\Delta f_1$, $\Delta R_1$) and corrugated ($\Delta f_2$, $\Delta R_2$) apparatuses after immersion; liquid properties are then determined from Eqs. 6–8.

Figure 5:
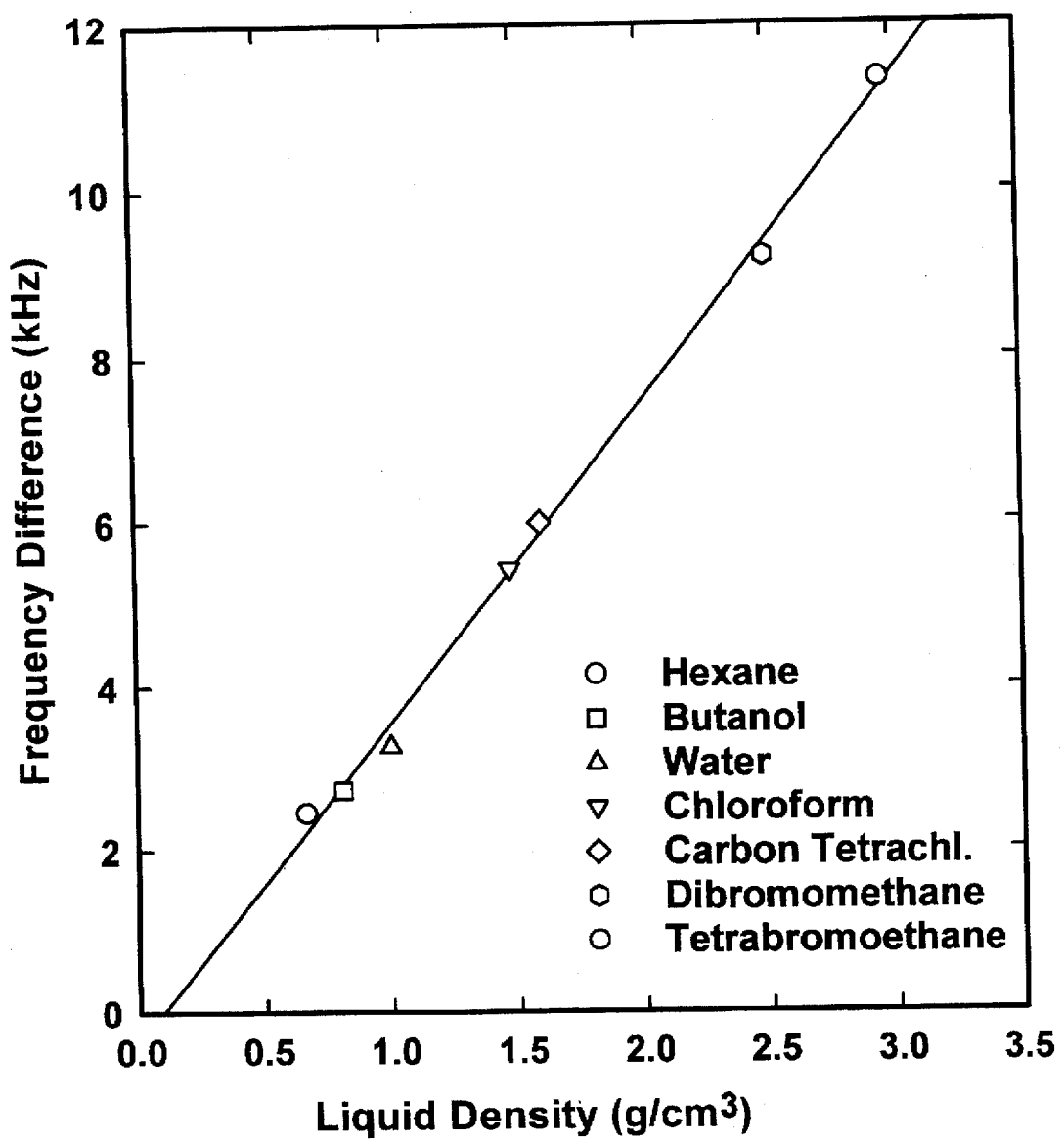
FIG. 5 is a graph of the difference in responses ($\Delta f_1 - \Delta f_2$) measured between smooth and corrugated resonators in certain liquids vs. liquid density.

FIG. 5 illustrates the densitometer function of the dual-resonator sensor of FIG. 2a. The difference in responses ($\Delta f_1 - \Delta f_2$) measured between the smooth and corrugated resonators upon immersion (two-sided liquid contact) is shown vs. liquid density in certain liquids. The response difference is extremely linear with density, following Eq. (6) when $c_1 = c_1$, despite variations in viscosity between the test liquids. The test liquids used were hexane L1, butanol L2, water L3, chloroform L4, carbon tetrachloride L5, dibromomethane L6, and tetrabromoethane L7.

Figures 6A, 6B:
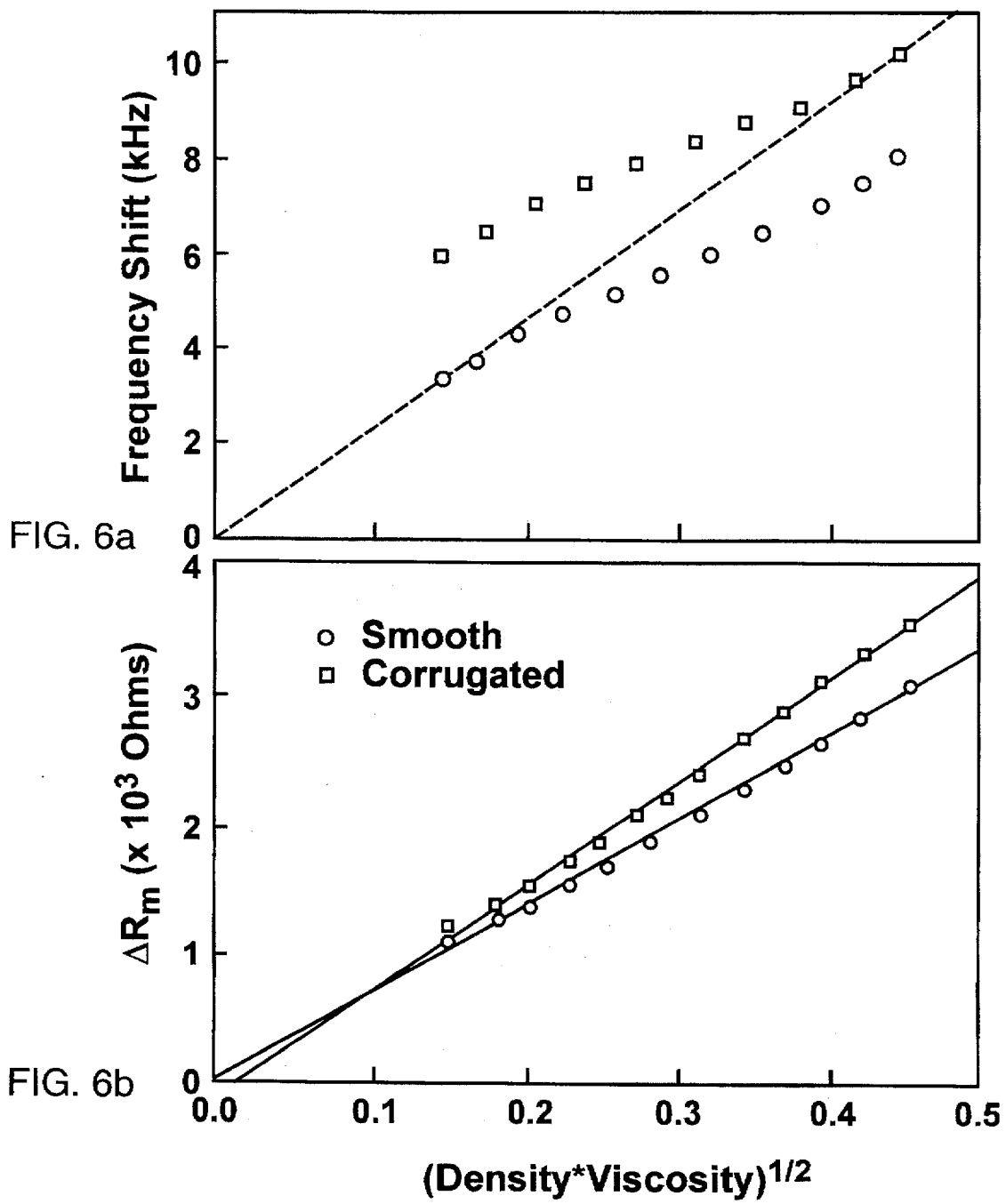
FIG. 6a is a graph of changes in oscillation frequencies for smooth and corrugated resonators vs. liquid parameter $(\rho\eta)^{1/2}$.
FIG. 6b is a graph of motional resistances for smooth and corrugated resonators vs. liquid parameter $(\rho\eta)^{1/2}$.

FIGS. 6a and 6b illustrate the viscometer function of the dual-resonator sensor of FIG. 2a. The variations in oscillation frequency and motional resistance ($\Delta R_m$) for the smooth and corrugated resonators are shown vs. the liquid parameter $(\rho\eta)^{1/2}$. In FIG. 6a, the network analyzer data (dashed line) indicate that $f_s$ varies linearly with $(\rho\eta)^{1/2}$, as expected from Eq. 2. The oscillator follows $f_s$ at low values of damping, but deviates as damping increases, introducing a non-linear response in $\Delta f$ vs. $(\rho\eta)^{1/2}$. FIG. 6b indicates that the oscillators are capable of driving the resonators for $\Delta R_m$ values up to approximately 3.5 k$\Omega$. $\Delta R_m$ increases more linearly with the damping parameter $(\rho\eta)^{1/2}$ and is thus a good alternative to using $\Delta f_s$ for extracting liquid viscosity.

An alternate method for determining density and viscosity can be utilized. This method is based on measuring the liquid-contacted device over a range of frequencies and fitting these measurements to an equivalent circuit model to extract liquid properties (density and viscosity). When quartz resonators 12 and 14 of FIG. 2a are excited at resonance, their surfaces execute a shear motion that interacts mechanically with a contacting liquid. The electrical response of the apparatus is thus determined, in part, by the mechanical impedance $Z_s$ at the solid-liquid interface. An equivalent circuit model to extract this surface mechanical impedance from the measured electrical response is indicated in FIG. 7.

Figure 7:
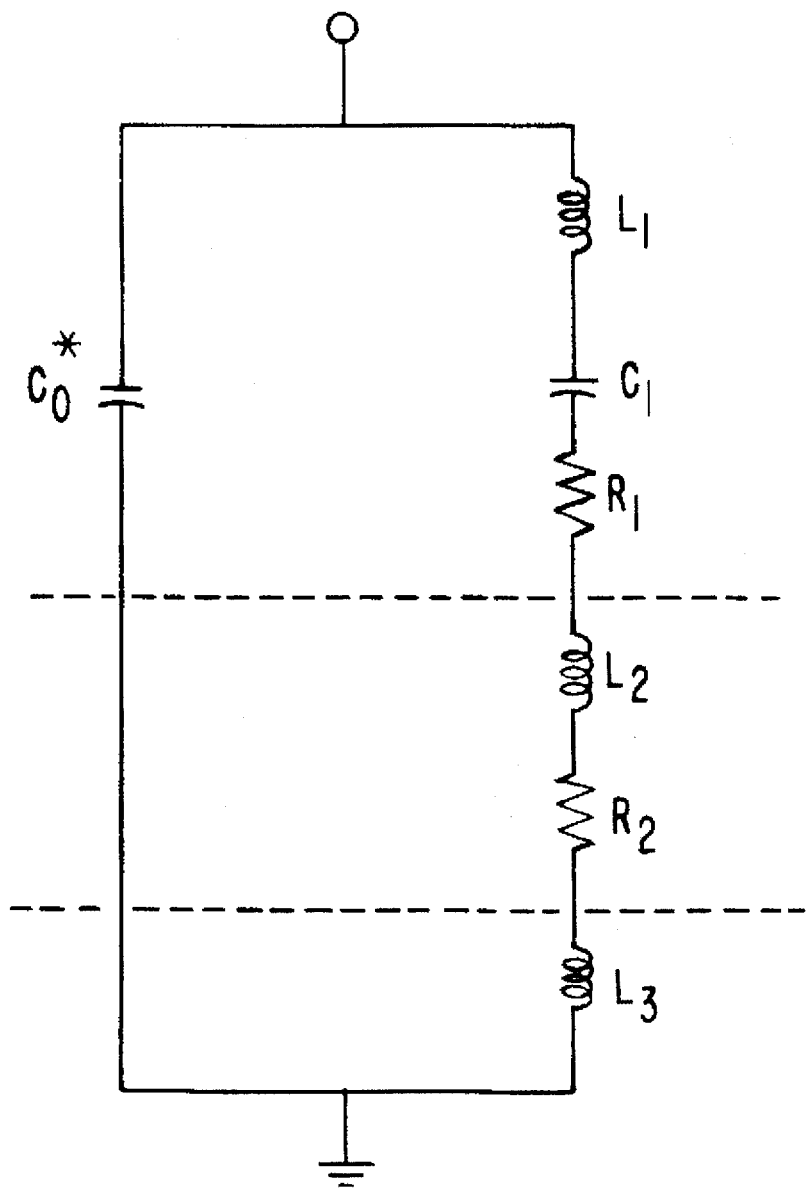
FIG. 7 is an equivalent circuit model of the electrical characteristics of a quartz resonator in contact with liquid.

In the equivalent circuit model of FIG. 7, a "static" capacitance $C_o$ arises between the electrodes located on opposite sides of the insulating quartz. Since $C_o$ appears in parallel with the ever-present arasitic capacitance $C_p$ in the test fixture, these two parameters are combined in the model: $C_o^* = C_o + C_p$. since the quartz is piezoelectric, electrical coupling to a shear-mode mechanical resonance gives rise to an additional "motional" contribution in parallel with the static capacitance. This motional arm has inductive ($L_1$), capacitive ($C_1$), and resistive ($R_1$) elements and the complex element $Z_o$ which depends on $Z_s$.

The elements of the equivalent circuit model are determined by fitting the model to electrical measurements made on a resonator over a range of frequencies near resonance. The electrical characteristics of the resonator can be given in terms of the electrical admittance, Y(f), defined as the ratio of current flow to applied voltage. Measurements of electrical admittance vs. frequency can be made with a network analyzer, impedance analyzer or other instruments that determine both amplitude and phase of the ratio of current flow through the apparatus to voltage applied (or the reciprocal). The elements of the equivalent circuit model are determined when the circuit admittance most closely agrees with the measured Y-vs.-f data. The circuit admittance is given by:

$$Y(f) = j\omega C_o^* + \frac{1}{Z_m} \quad (9)$$

where the "motional impedance" $Z_m$ is given by $$Z_m = R_1 + j\omega L_1 + \frac{1}{j\omega C_1} + Z_e \tag{10}$$

The elements $C_o^*$, $L_1$, $C_1$, and $R_1$ are determined by fitting the model to measurements made on the resonator before immersion in liquid ($Z_e$=0 in this case). The element $Z_e$ arises due to the interaction of the resonator with a contacting liquid. Consequently, fitting measurements made on the immersed apparatus to the circuit in FIG. 7 allows determination of the electrical impedance element $Z_e$ where $Z_q$ is the quartz characteristic shear wave impedance; this, in turn, is related to the surface mechanical impedance $Z_s$ from the equation:

$$Z_e = \frac{N\pi}{4K^2 \omega_s C_o} \left(\frac{Z_s}{Z_q}\right) \tag{11}$$

The surface mechanical impedance contains information regarding the energy stored and dissipated at the solid-liquid interface and is strongly influenced by the surface roughness and liquid trapping by this rough surface.

Figure 8:
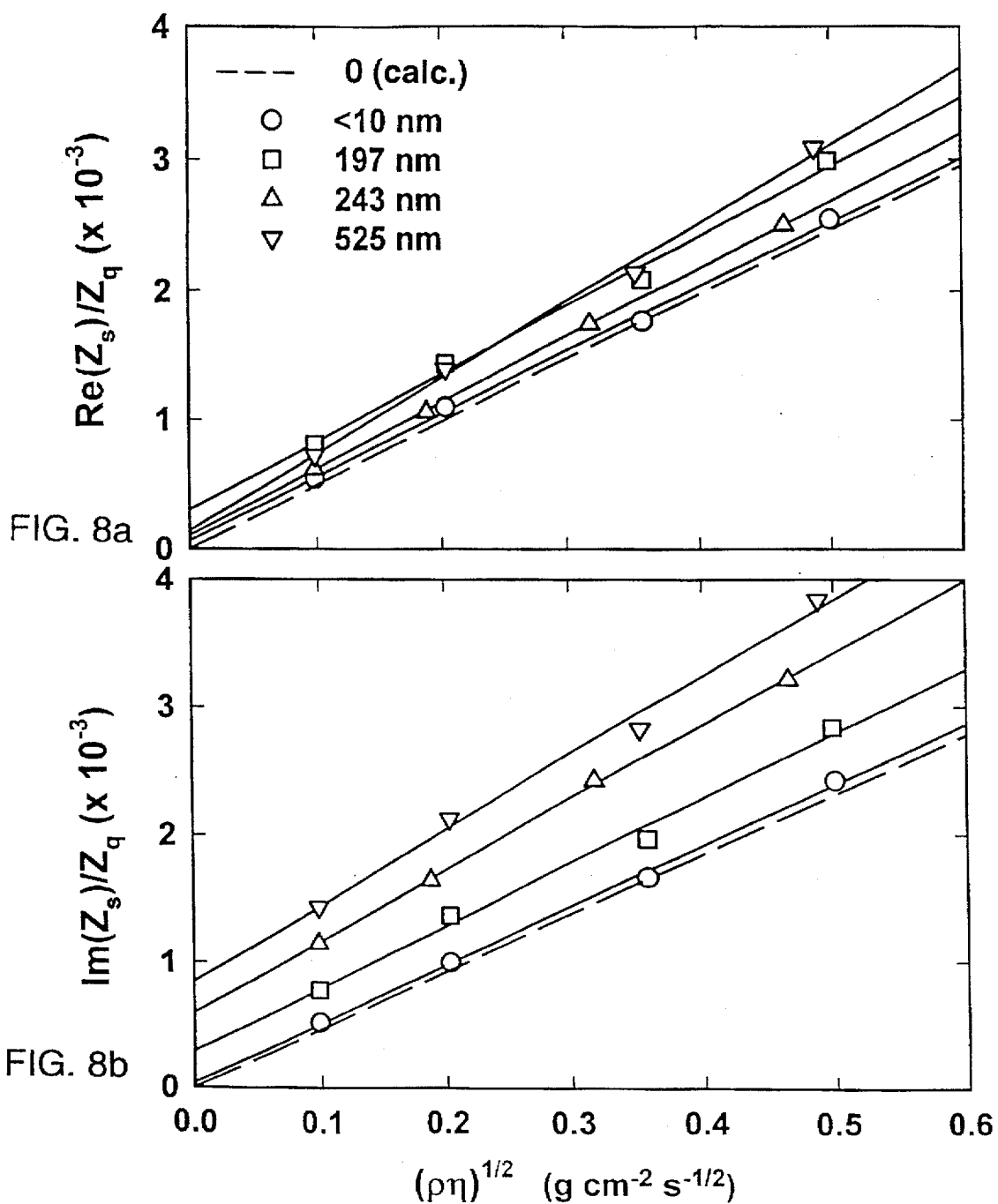
FIG. 8a is a graph of the real component of the ratio of surface mechanical impedance, $Z_s$, to quartz characteristic impedance, $Z_q$, for resonators with different surface roughness.
FIG. 8b is a graph of the imaginary component of the ratio of surface mechanical impedance, $Z_s$, to quartz characteristic impedance, $Z_q$, for resonators with different surface roughness.

FIGS. 8a and 8b indicate the real (Re) and imaginary (Im) parts of the surface mechanical impedance extracted from measurements made on several resonators in contact with liquids of various density and viscosity. The average roughness of the resonators, measured with a surface profilometer, varied from <10 to 445 nm. It is apparent that the surface mechanical impedance increases with liquid density $\rho$ and viscosity $\eta$ as well as with surface roughness. One interaction mechanism that results in this dependence on $\rho$ and $\eta$ is the viscous coupling to the moving resonator surface. It is seen that the results for the smoothest surface are in good agreement with the predictions of the equivalent circuit model for viscous coupling only (dashed lines in FIGS. 8a and 8b). This fact enables a smooth resonator (12 of FIG. 2a) to be used to extract the density-viscosity product ($\rho\eta$).

The offsets seen in the real and imaginary parts of the surface mechanical impedance correlate with the surface roughness of the apparatus, particularly the imaginary component. This imaginary component, which represents stored energy, has an offset that arises from the kinetic energy of the liquid trapped in crevices in the rough surface of resonator 14 of FIG. 2a. This offset is found to be proportional to the product of the liquid density and the surface roughness, the latter dictating the effective thickness of the trapped liquid layer. The difference between Im($Z_s$)/$Z_q$ measured with rough and smooth resonator surfaces 12 and 14 can thus be used to measure liquid density, while measurements made with smooth surface resonator 12 alone indicates $\rho\eta$. Thus, enough information is present to simultaneously determine $\rho$ and $\eta$. The real component of the mechanical impedance, representing power dissipation, also has an offset that is due to compressional wave generation by the shear motion of the randomly rough surface in contact with the liquid. As shown previously, it is possible to get trends which are more consistent with roughness using specially prepared textured surfaces (e.g., using photolithographic techniques or the like) rather than the randomly rough surfaces generated in polishing.

The experimental results of FIGS. 8a and 8b indicate that the mechanical impedance $Z_s$ arising from the interaction of either a smooth or rough resonator with a contacting liquid can be described as follows:

$$Re(Z_s)/Z_q = K_1 \sqrt{\rho\eta} + K_2 \rho \tag{12}$$

$$Im(Z_s)/Z_q = K_3 \sqrt{\rho\eta} + K_4 \rho \tag{13}$$

where $K_1$ through $K_4$ are constants. The imaginary part of $Z_s$ represents kinetic energy of liquid moved by the oscillating crystal surface; the first term represents viscously entrained liquid, while the second represents liquid trapped in crevices in a rough surface. The real part of $Z_s$ represents power dissipation at the solid/liquid interface; the first term arises from viscous dissipation, while the second term is due to compressional wave generation by surface irregularities. It is noted from FIGS. 8a and 8b that the offsets in the real and imaginary $Z_s$ plots, equal to the values of $c_2$ and $c_4$, are proportional to the surface roughness of the crystal.

It is also noted in FIGS. 8a and 8b that the offsets are more consistently related to surface roughness with the imaginary component of $Z_s$ than the real part. Consequently, measuring this component for a pair of smooth and rough resonators in contact with liquid provides a means for extracting liquid density and viscosity. To illustrate the extraction of liquid properties in this way, consider the mechanical impedances $Z_s^{(s)}$ and $Z_s^{(r)}$ associated with smooth and rough resonators contacting a liquid. Letting $z_1 = Im(Z_s^{(r)})/Z_q$ and $z_2 = Im(Z_s^{(s)})/Z_q$, Eq. (13) implies:

$$z_1 = c_{11}\sqrt{\rho\eta} + c_{12}\rho \tag{14}$$

$$z_2 = c_{21}\sqrt{\rho\eta} + c_{22}\rho \tag{15}$$

where $c_{ij}$ are constants. Since the resonators have different roughness, $c_{12} \neq c_{22}$, and measurement of the quantities Im($Z_s^{(s)}$)/$Z_q$, Im($Z_s^{(r)}$)/$Z_q$ permits a unique determination of $\rho$ and $\eta$.

Eqs. (14) and (15) can be solved for $\rho$ and $\eta$ in terms of $z_1$ and $z_2$ measured for the smooth and rough apparatuses in contact with a liquid:

$$\rho = \frac{c_{21}z_1 - c_{11}z_2}{c_{12}c_{21} - c_{11}c_{22}} \tag{16}$$

$$\eta = \frac{(z_2 - c_{22}\rho)^2}{c_{21}^2 \rho} \tag{17}$$

Solving Eq. (16) for $\rho$ and then substituting this value into Eq. (17) yields $\eta$.

A couple of notes should be added regarding this technique for extracting liquid density and viscosity. In the discussion above, it describes using the impedance factors $Z_s/Z_q$, extracted by curve-fitting electrical measurements made over a range of frequencies on the resonators, to determine the liquid properties. It can be shown, however, that the surface impedances contributed by liquid contact cause a proportional change in resonant frequency and damping:

$$\Delta f = f_2 - f_1 = \frac{-f_1}{\frac{N}{90}} Im\left(\frac{Z_s}{Z_q}\right) \tag{18}$$

$$\frac{1}{Y_2} - \frac{1}{Y_1} = \frac{N\pi}{4K^2 \omega_s C_o} Re\left(\frac{Z_s}{Z_q}\right) \tag{19}$$

where $f_1$ and $Y_1$ denote the resonant frequency and admittance magnitude at resonance before immersion while $f_2$ and $Y_2$ denote these quantities after immersion. Eqs. 18 and 19 indicate that rather than measuring the resonator characteristics over a range of frequencies, and fitting these data to extract $Z_s/Z_q$, one could simply use an oscillator circuit to track changes in the resonant frequencies and peak heights upon immersion to determine $Z_s/Z_q$. If only the imaginary component is needed, it is sufficient to track only the changes in resonant frequency for a rough and smooth apparatus upon immersion. Using Eqs. 18 and 19 to determine $z_1$ and $z_2$, Eqs. 14 and 15 can be applied to determine the calibration coefficients ($c_{ij}$). Then Eqs. 16 and 17 can be used to extract $\rho$ and $\eta$ from measurements made on unknown liquids. In fact, in light of Eqs. 18 and 19, $\rho$ and $\eta$ can be extracted simply by defining $z_1$ and $z_2$ as the frequency shifts, $\Delta f$, measured with the rough and smooth resonators due to liquid contact and applying Eqs. 14, 15, 16 and 17. This technique of using oscillators to drive the quartz resonators, and monitoring oscillation frequency alone, would be less expensive and easier to implement in a practical system than using a network analyzer, as described above.

In yet another alternative embodiment, it is not necessary to use a pair of resonators to separate the density from viscosity. Referring to Eqs. 12 and 13, measurements of $\text{Re}(Z_s)/Z_q$ and $\text{Im}(Z_s)/Z_q$, either by a swept-frequency measurement and curve-fitting or from frequency shift and admittance peak measurements (Eqs. 14 and 15), made on a single roughened apparatus (with $c_2 \ne c_4$) is sufficient to extract both liquid density and viscosity.

The additional information provided by using both $\text{Re}(Z_s)/Z_q$ and $\text{Im}(Z_s)/Z_q$ for both a smooth and a rough apparatus leads to improved accuracy in the evaluation of $\rho$ and $\eta$. It is useful to use two or more apparatuses with varying roughness to improve the accuracy of the evaluation of $\rho$ and $\eta$.

For conductive liquids only one side of the quartz resonator should be immersed to prevent the generation of conduction currents in the contacting liquid. For non-conductive liquids, both sides can be immersed. Because the entrained or trapped liquid layer is very thin (approximately 250 nm in water at 5 MHZ and 20° C.), only a small amount of liquid in contact with the surface of the resonator is required to measure liquid properties between the two surface electrodes.

Surface texturing of resonator 14 of FIG. 2a can be accomplished in a number of ways. These include, but are not limited to, using a rough grit to polish the quartz (before the electrode is deposited), sandblasting, photolithography of already deposited layers, affixing particles to the surface, ion milling into quartz or metal, or using electrodeposition to deposit a rough surface electrode. From the previous discussion, the roughness features must be on the order of 250 nm or larger to trap an effective liquid thickness comparable to that viscously entrained. For more reproducible texturing, standard photolithographic processing can be used to form miniature corrugations on the apparatus surface. The resonator sensors can be packaged such that one or both sides of the apparatus are in contact with the liquid, and RF connections 112 and 114 can be made to the apparatus.

Figure 9:
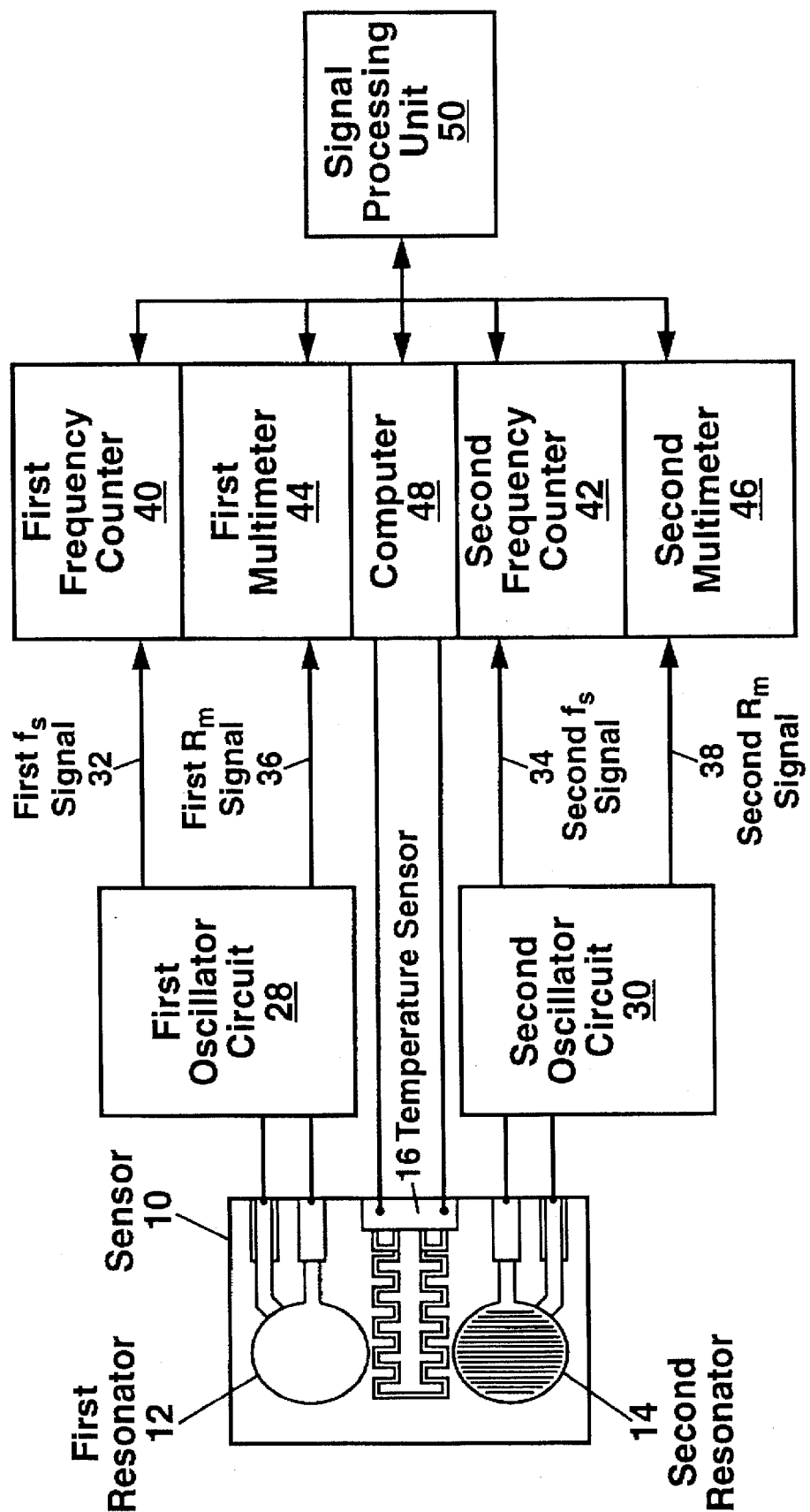
FIG. 9 is an alternative embodiment of the invention with a temperature measuring apparatus.

FIG. 9 shows how temperature monitor 16 can be added alongside the resonators so that the temperature at which fluid properties are measured can be determined. Signal processing unit 50 is included to evaluate density and viscosity from the frequency shifts and/or amplitude of the two oscillators 28 and 30 and temperature from the meander-line resistance change of the monitor 16.

Figure 10:
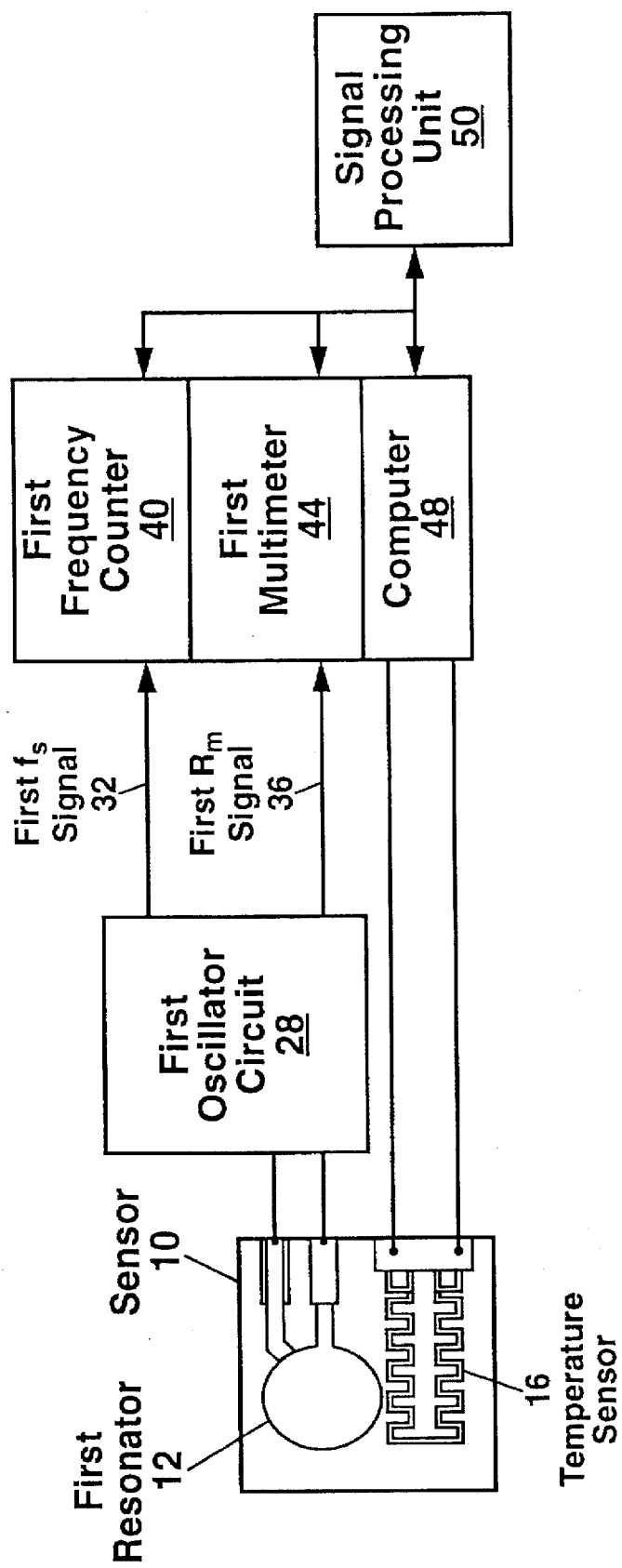
FIG. 10 is a preferred embodiment of the oil condition monitor for measuring the density-viscosity product.

Another embodiment can be used to provide real-time in situ monitoring of the density-viscosity product which indicates some aspects of the condition of fluids, such as engine oil. The ultrasonic sensor for monitoring oil density-viscosity product comprises a single smooth surfaced quartz resonator 12 with accompanying temperature monitor 16 (FIG. 10). The apparatus can be designed in such a way that electrical measurements indicate the density-viscosity product of a contacting fluid. These measurements include monitoring changes in the acoustic resonant frequency and the admittance magnitude. It is possible to extract enough information from a single measurement of admittance magnitude to determine fluid condition.

Determining both viscosity and density or the product of density and viscosity ($\rho\eta$) using an in situ probe can be successfully applied in a variety of areas. For example, it can be used to monitor the condition of lubricating oil in a combustion engine or oil condition in other systems such as transformers, pumps, or other machinery. Other automobile fluids can also be monitored including engine coolants or battery electrolyte. For engine coolants, the standard method of evaluating the thermal quality is solution density, making the density measurement capability a key one. In lead-acid batteries, the state of charge is monitored by measuring the concentration of the sulfuric acid in the electrolyte solution. Electrolyte density and viscosity both correlate with acid content. Additional applications can also include monitoring process and waste streams.

Although the description of the invention above refers to specific applications in the automotive industry, there are several other applications for this technology. The disclosure is for all applications whereby viscosity and density or fluid conditions are monitored. These include, but are not limited to monitoring and/or control of:

1) Working fluids in machines, including liquid refrigerants (in air conditioners, heat pumps, and refrigeration machinery), hydraulic fluids (brake systems, actuators in airplanes, etc.), and cooling fluids (in heat exchangers, radiators, etc.).

2) Fluids used as lubricants in engines, compressors, electric motors, cutting and other machining tools.

3) Liquid fuels in internal combustion engines, aircraft engines, rockets, etc.

4) Industrial blending or mixing applications, where solids are combined with a liquid, or two or more liquids are combined. The density and/or viscosity can be used to indicate the relative concentration of one solid or liquid dissolved in another. The blending of fuels, paints, or lubricants are examples.

5) Food processing or preparation, including monitoring of cooking oils, fats and emulsifiers.

6) Industrial chemical processes liquid density and viscosity of fluids in a chemical process can be used to control chemical production facilities. Plating processes and other processes using fluid streams with high salt concentration are preferred applications due to the large density and viscosity changes that occur as salt concentration changes.

7) Plastics and composite manufacturing to control proportions of resin and hardener, as well as monitoring the curing process.

8) Medical applications, including the monitoring of body fluids for diagnostic-applications.

9) Supercritical fluid chromatography and extraction processes, where the fluid density is varied to enable separations.

10) Laboratory process, including phase change indication, physical identification of chemicals, etc.

11) Non-newtonian fluids.

INDUSTRIAL APPLICABILITY

The invention is further illustrated by the following non-limiting examples.

EXAMPLE I

Figure 12A:
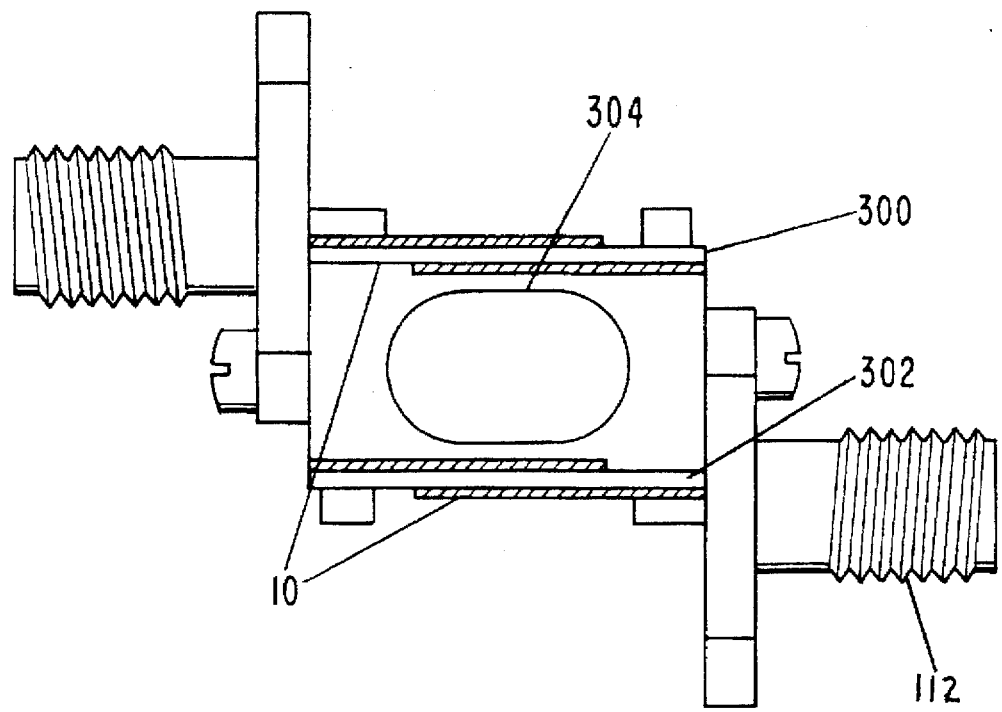
FIGS. 12a and 12b are side and top views, respectively.
Figure 12B:
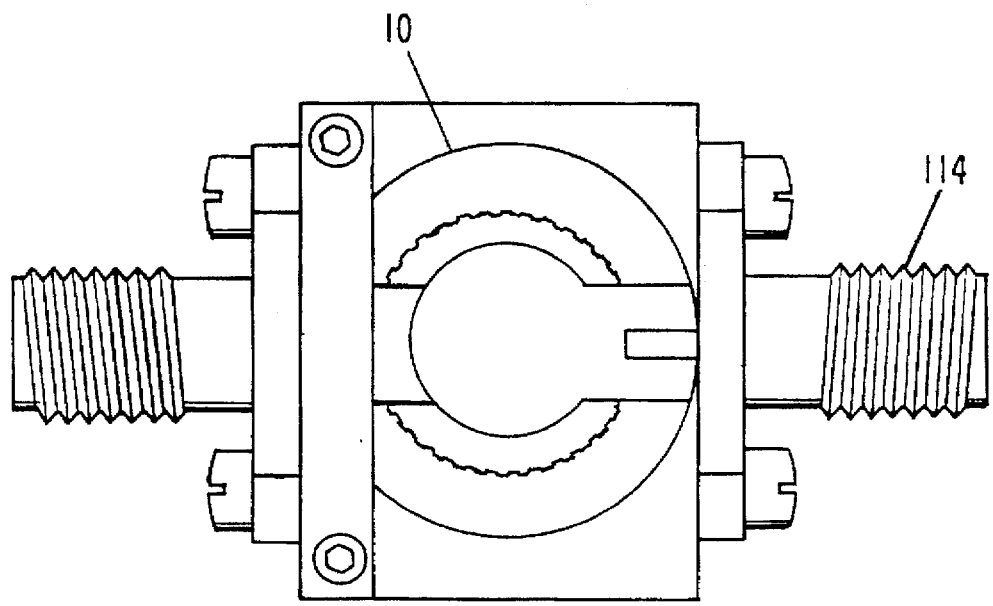

The preferred apparatus and method was constructed and employed to determine liquid density and viscosity using a test fixture, illustrated in FIGS. 12a and 12b, that holds two quartz resonators (one smooth 300 and one rough 302) in contact with liquid sample 304. A network analyzer was used to measure the electrical characteristics of each apparatus 300 and 302 over a range of frequencies near the fundamental resonance before and after liquid sample 304 was added. Fitting these measurements to the equivalent circuit model of FIG. 7, and applying Eqs. 9–11, allowed extraction of $Z_s/Z_q$ for each resonator 300 and 302. Measuring these characteristics with liquids 304 of known density and viscosity, and fitting these data to Eqs. 14 and 15, allowed determination of $c_{11}$, $c_{12}$, $c_{21}$, and $c_{22}$, thereby calibrating resonators 300 and 302. These constants were then used in Eqs. 16 and 17 to determine the density and viscosity of unknown liquids from electrical measurements. This analysis was performed on the set of calibration measurements (using liquids of known density and viscosity) in order to compare the extracted and known liquid properties.

Figure 11:
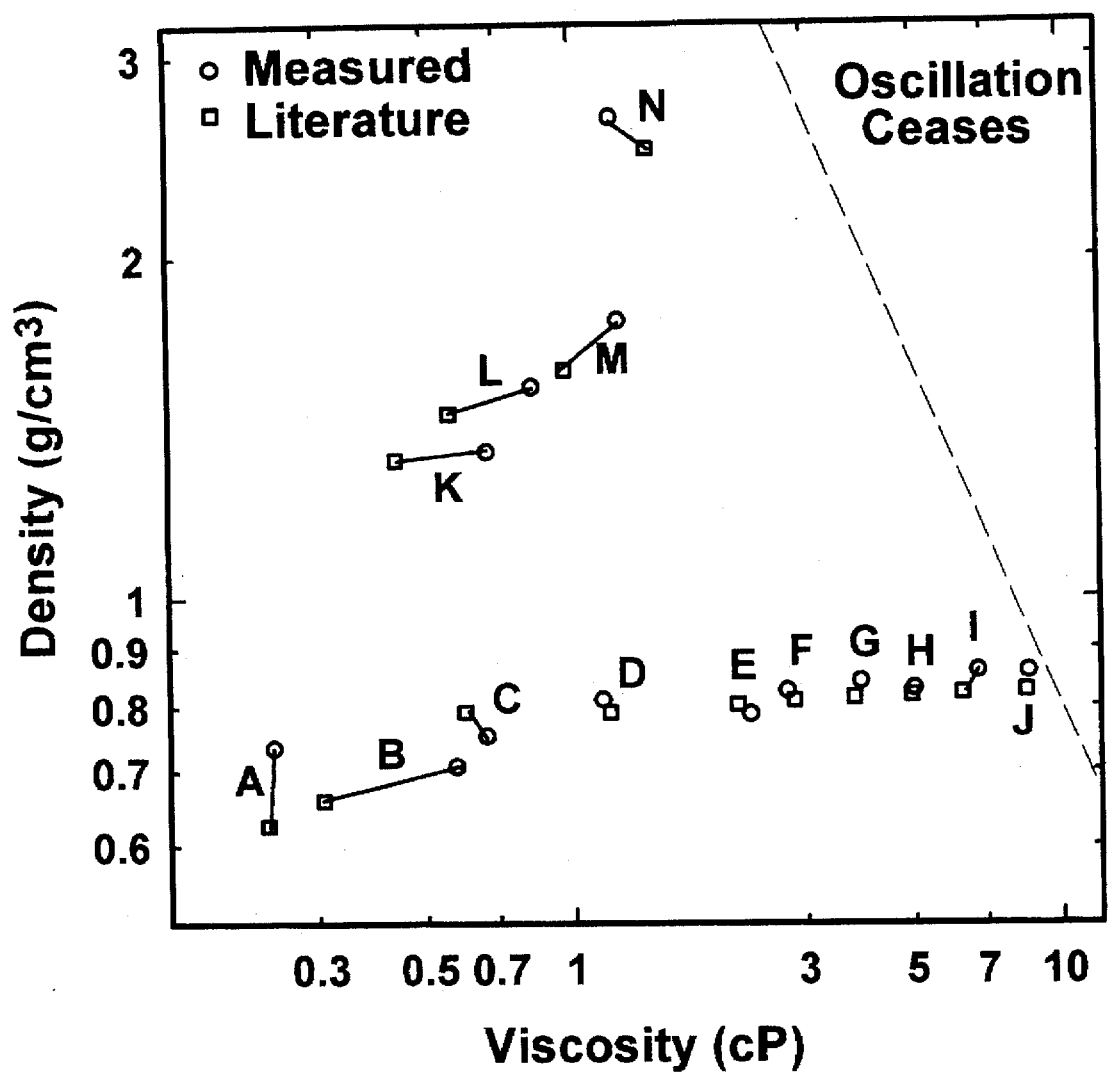
FIG. 11 is a "scatter diagram" of measurements with the preferred embodiment for different liquids compared to literature values.

FIG. 11 shows a comparison of the known (literature values) and extracted values of liquid density and viscosity for several organic solvents. The outputs as measured by the dual-resonator are represented by closed circles with literature values shown as squares. The liquid corresponding to each set of points is indicated in Table I. With 2-sided liquid contact, the crystal became damped too severely to sustain oscillation for $\rho\eta > 8$. Since liquid damping increased (Eq. 3) as $n(\rho\eta)^{1/2}$, limiting liquid contact to a single side extended the $\rho\eta$ range to 32. The viscosities varied over a range of 80, while densities spanned a range of 3.8. The average differences between the measured and literature values were 5.3% for density and 19.5% for viscosity.

TABLE 1

| | |
|---|---|
| A n-pentane | H n-hexanol |
| B n-hexane | I n-heptanol |
| C methanol | J n-octanol |
| D ethanol | K dichloromethane |
| E n-propanol | L trichloroethylene |
| F n-butanol | M carbon tetrachloride |
| G n-pentanol | N dibromomethane |

EXAMPLE II

Figure 13:
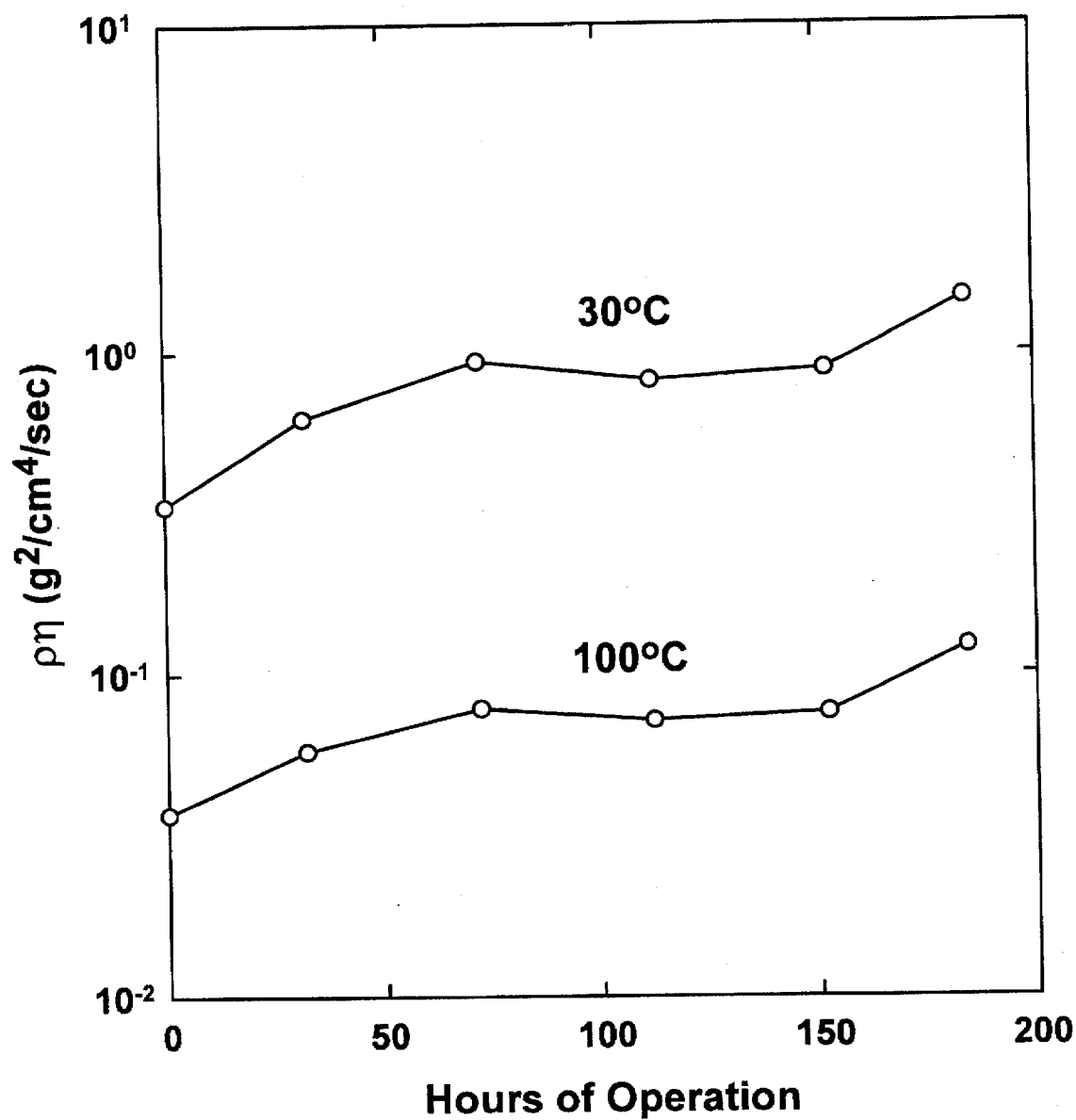
FIG. 13 is a graph of the density-viscosity product ($\rho\eta$) of vehicle crankcase oil vs. engine run time at two different temperatures.

A single smooth surfaced ultrasonic sensor of FIG. 10 was tested using oil samples drawn at periodic intervals from an engine dynamometer test. A single smooth sensor was successively immersed in each of six samples and measurements were successively made at constant oil temperatures 30° C. and 100° C. A network analyzer was used to extract parameters from the sensor. The density-viscosity product extracted from these measurements is shown in FIG. 13 as a function of the elapsed operating time. A general increase in the density-viscosity product is observed as use time increases. The changes are most pronounced near the end of the useful life of the oil (beyond 150 hours). The dip in the curve resulted from addition of new oil during the dynamometer test to replace oil that has been drawn for sampling (causing a decrease in the average oil life).

A number of other parameters were extracted from measurements made on the ultrasonic sensor when it was submersed in a fluid. These include frequency shift, $\Delta f$, and motional resistance and inductance. All of these parameters, extracted from measurements made at 30° and 100° C. are shown in Tables II and III.

TABLE II

Parameters extracted from ultrasonic sensor measurements made on engine oil at 30° C. drawn after various time intervals.

| Run Time (hrs) | Resistance (Ohm) | $\Delta f$ (kHz) | Inductance ($\mu$H) | $\rho\eta$ ($g^2/cm^4$-s) |
|---|---|---|---|---|
| 0 | 4067 | −14.5 | 130 | 0.333 |
| 32 | 5547 | −20.6 | 178 | 0.623 |
| 72 | 6864 | −25.1 | 220 | 0.939 |
| 112 | 6338 | −22.1 | 203 | 0.819 |
| 152 | 6595 | −23.0 | 211 | 0.887 |
| 184 | 8539 | −31.1 | 273 | 1.475 |

TABLE III

Parameters extracted from ultrasonic sensor measurements made on engine oil at 100° C. drawn after various time intervals.

| Run Time (hrs) | Resistance (Ohm) | $\Delta f$ Shift (kHz) | Inductance ($\mu$H) | $\rho\eta$ ($g^2/cm^4$-s) |
|---|---|---|---|---|
| 0 | 1351 | −4.30 | 43.2 | 0.0367 |
| 32 | 1685 | −5.10 | 53.9 | 0.0576 |
| 72 | 1984 | −6.09 | 63.5 | 0.0783 |
| 112 | 1874 | −5.57 | 60.0 | 0.0718 |
| 152 | 1929 | −6.53 | 61.8 | 0.0759 |
| 184 | 2449 | −8.09 | 78.4 | 0.1210 |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. An apparatus for real-time in situ measurement of fluid density and viscosity comprising:
   a first resonator comprising a smooth surface;
   a second resonator comprising a textured surface;
   first measuring means connected to at least one of the first and second resonators for measuring density of a fluid disposed on said resonators; and
   second measuring means connected to at least one of the first and second resonators for measuring viscosity of the fluid disposed on said resonators.

2. The apparatus of claim 1 wherein said first resonator comprises means for providing a product of density and viscosity of the fluid.

3. The apparatus of claim 1 wherein said second resonator comprises means for providing a sum of a product of density and viscosity of the fluid plus a quantity which is proportional to density and effective thickness of the trapped fluid.

4. The apparatus of claim 1 wherein said first measuring means comprises means for comparing outputs of said resonators.

5. The apparatus of claim 4 wherein said means for comparing outputs of said resonators comprises means for eliminating viscosity dependence.

6. The apparatus of claim 5 wherein said second measuring means comprises said first measuring means and an output of said first resonator.

7. The apparatus of claim 5 wherein second measuring means comprises said first measuring means and an output of said second resonator.

8. The apparatus of claim 1 wherein said first and second measuring means comprises means for measuring electrical responses of first and second resonators.

9. The apparatus of claim 8 wherein said means for measuring electrical responses comprises means for measuring resonant frequencies (f).

10. The apparatus of claim 8 wherein said means for measuring electrical responses comprises means for measuring crystal damping ($\Delta R_m$).

11. The apparatus of claim 8 wherein said means for measuring electrical responses comprises means for measuring electrical responses selected from the group consisting of admittance, impedance, reflection, and combinations thereof.

12. The apparatus of claim 8 wherein said means for measuring electrical responses comprises oscillator means.

13. The apparatus of claim 8 wherein said means for measuring electrical responses comprises means for measuring changes in said electrical responses in a calibrating medium and upon disposition of the fluid.

14. The apparatus of claim 1 wherein said first resonator comprises a surface to minimize fluid trapping.

15. The apparatus of claim 1 wherein said first resonator comprises a surface whereby an effective thickness of the trapped fluid is lass than a liquid decay length (h<$\delta$) of the fluid.

16. The apparatus of claim 1 wherein said second resonator comprises a surface that traps a fixed quantity of the fluid.

17. The apparatus of claim 1 wherein said second resonator comprises means for texturing said textured surface to optimize an output of said second resonator.

18. The apparatus of claim 1 wherein said second resonator comprises means for orienting ridges perpendicular to a direction of surface shear displacement.

19. The apparatus of claim 1 wherein said second resonator comprises a uniformly textured surface.

20. The apparatus of claim 19 wherein said uniformly textured surface comprises photolithographic means.

21. The apparatus of claim 1 further comprising means for measuring a temperature of the fluid.

22. The apparatus of claim 1 further comprising means for preventing contamination buildup on said resonator surfaces.

23. The apparatus of claim 1 wherein said resonators comprise piezoelectric substrate means operating in a thickness shear mode.

24. The apparatus of claim 1 further comprising a monolithic structure.

25. A method for real-time in situ measurement of fluid density and viscosity, the method comprising the steps of:
a) providing a first resonator comprising a smooth surface;
b) providing a second resonator comprising a textured surface;
c) measuring density of a fluid disposed on the resonators; and
d) measuring viscosity of the fluid disposed on the resonators.

26. The method of claim 25 wherein the step of providing a first resonator comprises the resonator providing a product of density and viscosity of the fluid.

27. The method of claim 25 wherein the step of providing a second resonator comprises the resonator providing a sum of a product of density and viscosity of the fluid plus a quantity which is proportional to density and effective thickness of trapped fluid.

28. The method of claim 25 wherein the step of measuring density comprises comparing the outputs of the resonators.

29. The method of claim 28 wherein the step of comparing outputs of the resonators comprises eliminating viscosity dependence.

30. The method of claim 25 wherein the step of measuring viscosity comprises measuring density and an output of the first resonator.

31. The method of claim 25 wherein the step of measuring viscosity comprises measuring density and an output of the second resonator.

32. The method of claim 25 wherein the step of measuring density and viscosity comprises measuring electrical responses of the resonators.

33. The method of claim 32 wherein the step of measuring electrical responses comprises measuring resonant frequencies (f).

34. The method of claim 32 wherein the step of measuring electrical responses comprises measuring crystal damping ($\Delta R_m$).

35. The method of claim 32 wherein the step of measuring electrical responses comprises measuring electrical responses selected from the group consisting of admittance, impedance, reflection, and combinations thereof.

36. The method of claim 32 wherein the step of measuring electrical responses comprises providing oscillators.

37. The method of claim 32 wherein the step of measuring electrical responses comprises measuring changes in the electrical responses in a calibrating medium and upon disposition of the fluid.

38. The method of claim 25 wherein the step of providing a first resonator comprises providing a surface to minimize fluid trapping.

39. The method of claim 25 wherein the step of providing a first resonator comprises providing a surface whereby an effective thickness of the trapped fluid is less than a liquid decay length (h<$\delta$) of the fluid.

40. The method of claim 25 wherein the step of providing a second resonator comprises providing a surface that traps a fixed quantity of the fluid.

41. The method of claim 25 wherein the step of providing a second resonator comprises texturing the textured surface to optimize an output of the second resonator.

42. The method of claim 25 wherein the step of providing a second resonator comprises orienting ridges perpendicular to the direction of surface shear displacement.

43. The method of claim 25 wherein the step of providing a resonator comprises providing a uniformly textured surface.

44. The method of claim 43 wherein the step of providing a uniformly textured surface comprises utilizing a photolithographic process.

45. The method of claim 25 further comprising the step of measuring a temperature of the fluid.

46. The method of claim 25 further comprising the step of preventing contamination buildup on the resonator surfaces.

47. The method of claim 25 wherein the steps of providing resonators comprise providing a piezoelectric substrate operating in a thickness shear mode.

48. The method of claim 25 further comprising the step of providing a monolithic apparatus.

* * * * *